(12) United States Patent
Ahne (10) Patent No.: US 9,482,633 B2
(45) Date of Patent: Nov. 1, 2016

(54) CAPACITIVE MEASUREMENT MULTIPLEXING CIRCUIT AND METHOD

(71) Applicant: Lexmark International, Inc., Lexington, KY (US)

(72) Inventor: Adam Jude Ahne, Lexington, KY (US)

(73) Assignee: LEXMARK INTERNATIONAL, INC., Lexington, KY (US)

( * ) Notice: Subject to any disclaimer, the term of this patent is extended or adjusted under 35 U.S.C. 154(b) by 523 days.

(21) Appl. No.: 13/852,857

(22) Filed: Mar. 28, 2013

(65) Prior Publication Data

US 2013/0257459 A1  Oct. 3, 2013

Related U.S. Application Data

(60) Provisional application No. 61/618,317, filed on Mar. 30, 2012.

(51) Int. Cl.
*G01R 27/26* (2006.01)
*G01N 27/22* (2006.01)
*G03G 15/08* (2006.01)

(52) U.S. Cl.
CPC ............ *G01N 27/22* (2013.01); *G03G 15/086* (2013.01)

(58) Field of Classification Search
CPC .... G01R 27/2605; G01D 5/24; G01D 5/165; G01N 27/22; G01N 27/221; G01N 27/223; G01N 27/2635
USPC ................................ 324/658, 674, 683, 679
See application file for complete search history.

(56) References Cited

U.S. PATENT DOCUMENTS

| | | | | |
|---|---|---|---|---|
| 4,733,171 | A * | 3/1988 | Milkovic | 324/142 |
| 5,012,247 | A * | 4/1991 | Dillman | 341/172 |
| 5,659,254 | A * | 8/1997 | Matsumoto | G01D 5/2417 324/548 |
| 5,987,269 | A | 11/1999 | Allen et al. | |
| 6,452,514 | B1 * | 9/2002 | Philipp | G01D 5/2405 178/18.06 |
| 6,853,241 | B2 * | 2/2005 | Fujimoto | H03F 3/005 327/124 |
| 6,924,760 | B1 * | 8/2005 | McLeod | H03M 1/066 341/144 |

(Continued)

FOREIGN PATENT DOCUMENTS

JP    H01-144075 A    6/1989

OTHER PUBLICATIONS

L.K. Baxter, "Capacitive Sensors" Jun. 26, 2001, located at http://www.capsense.com/capsense-wp.pdf.

*Primary Examiner* — Jermele M Hollington
*Assistant Examiner* — Thang Le (57) ABSTRACT

A capacitance measuring system, including: a calibration capacitor; first circuitry for sensing an input current at an input thereof and generating an output signal that is based upon a capacitance appearing at the input of the first circuitry; and multiplexer circuitry, coupled between the input of the first circuitry and a terminal of each of the capacitor to be measured and the calibration capacitor, for selectively coupling the terminal of each, one at a time, to the input of the first circuitry while the terminal not coupled to the input of the conversion circuitry is coupled to a ground reference; and controller circuitry for calculating a capacitance of the capacitor to be measured based upon the output signal of the first circuitry when the capacitor to be measured is coupled to the input thereof and upon the output signal of the first circuitry when the calibration capacitor is coupled to the input thereof.

19 Claims, 5 Drawing Sheets

(56) References Cited

U.S. PATENT DOCUMENTS

| | | | |
|---|---|---|---|
| 6,949,937 B2 * | 9/2005 | Knoedgen | G01D 5/241 324/658 |
| 7,078,916 B2 * | 7/2006 | Denison | G01D 5/2417 324/661 |
| 7,555,231 B2 | 6/2009 | Etter et al. | |
| 8,283,934 B2 * | 10/2012 | Nishizono | H03K 17/962 324/658 |
| 8,570,052 B1 * | 10/2013 | Mahartya | G01R 27/2605 324/658 |
| 8,718,496 B2 | 5/2014 | Barry et al. | |
| 2002/0172521 A1 | 11/2002 | Oguma et al. | |
| 2003/0123888 A1 | 7/2003 | Naito et al. | |
| 2005/0099188 A1 * | 5/2005 | Baxter | 324/678 |
| 2007/0247171 A1 * | 10/2007 | O'Dowd et al. | 324/658 |
| 2008/0069576 A1 | 3/2008 | Etter et al. | |
| 2011/0074446 A1 * | 3/2011 | Chou | G06F 3/0418 324/679 |
| 2011/0163766 A1 * | 7/2011 | Geaghan | G06F 3/044 324/678 |
| 2011/0261005 A1 * | 10/2011 | Joharapurkar et al. | 345/174 |
| 2013/0257455 A1 | 10/2013 | Ahne et al. | |
| 2013/0278447 A1 * | 10/2013 | Kremin | 341/20 |

\* cited by examiner

CAPACITIVE MEASUREMENT MULTIPLEXING CIRCUIT AND METHOD

CROSS REFERENCES TO RELATED APPLICATIONS

The present application is related to and claims priority from U.S. provisional application 61/618,317, filed Mar. 30, 2012, entitled, "Capacitive Measurement Multiplexing Circuit and Method," the content of which is hereby incorporated by reference herein it is entirety.

The present application is related to U.S. patent application Ser. No. 13/340,789, filed Dec. 30, 2011, entitled, "Capacitive Toner Level Sensor," and U.S. patent application Ser. No. 13/432,693, filed Mar. 28, 2012, entitled, "Capacitive Supply Level Sensing Circuit and Method," the contents of such applications are hereby incorporated by reference herein in their entirety.

BACKGROUND

1. Technical Field

The present disclosure relates to imaging devices. More particularly, it relates to a circuit and method for measuring toner or ink levels in the imaging unit of an imaging device.

2. Description of the Related Art

Image forming devices such as copiers, laser printers, facsimile machines and the like typically use one or more toner containers to hold toner supply used for image forming processes. In some image forming devices, a large toner supply is provided in a reservoir in a toner cartridge that mates with a separate imaging unit. The imaging unit may include a developer unit having a sump that holds a smaller amount of toner, enough to ensure toner is adequately supplied by a toner adder roll and a developer roll, both of which are located in the developer unit, to a photoconductive drum. As toner within the imaging unit sump is depleted due to printing operations, additional toner is transferred from the toner cartridge to the imaging unit sump.

To ensure satisfactory operation of the imaging unit to transfer toner, the toner level within the imaging unit sump is maintained at a proper level. For example, if the imaging unit sump holds too much toner, toner may pack in the imaging unit sump, leak out of the ports and eventually break other components located inside and outside the imaging unit. If the toner level in the imaging unit sump gets too low, the toner adder roll may starve, causing a doctor blade of the imaging unit to film and damage the developer roll which may eventually impair the future performance of the imaging unit. As such, it is desirable to know the toner level in the imaging unit sump so as to effectively determine when to move toner from toner cartridge to the imaging unit sump.

Some methods for determining toner level in a container use estimates of toner use and accumulation based on print or time counts. However, these methods may not be accurate due to variability in factors such as the environment, developer roll age, toner patch sensing cycles, and toner transfer parameters.

Other known techniques for sensing or determining toner level include the use of electrical sensors that measure the motive force required to drive an agitator within a toner container, optical devices including mirrors and toner dust wipers in a container, and other opto-electromechanical devices such as a flag that moves with the toner level to actuate a sensor which triggers only when the toner volume reaches a predetermined level. Unfortunately, the addition of moving hardware increases component complexity and opportunities for errors. For instance, toner agitation may create unwanted toner dust in addition to the added complication of moving hardware.

Other techniques for sensing or determining toner level include use of a capacitive sensor disposed within a toner container, such as a waste toner container, and circuitry for sensing the capacitance of the capacitive sensor as toner levels in the container change. In one existing implementation, illustrated in FIG. 1, an AC signal generator 101 is connected to the capacitor Cx, representing the capacitive sensor to be measured, and applies a generally square wave signal thereto. Capacitor Cx couples the AC signal generator 101 to a high-pass amplifier 102 which buffers and amplifies the AC square wave signal. A synchronous rectifier 103, which is coupled to the output of the high pass amplifier 102, operates at the same frequency as AC signal generator and is synchronized thereto. The synchronous rectifier 103 converts the square-wave (bipolar) signal into a unipolar signal. A low-pass filter 104 receives the unipolar signal from the synchronous rectifier 103 and amplifies and smoothes the unipolar signal. The low pass filter 104 outputs a DC output voltage Vout.

Figure 1:
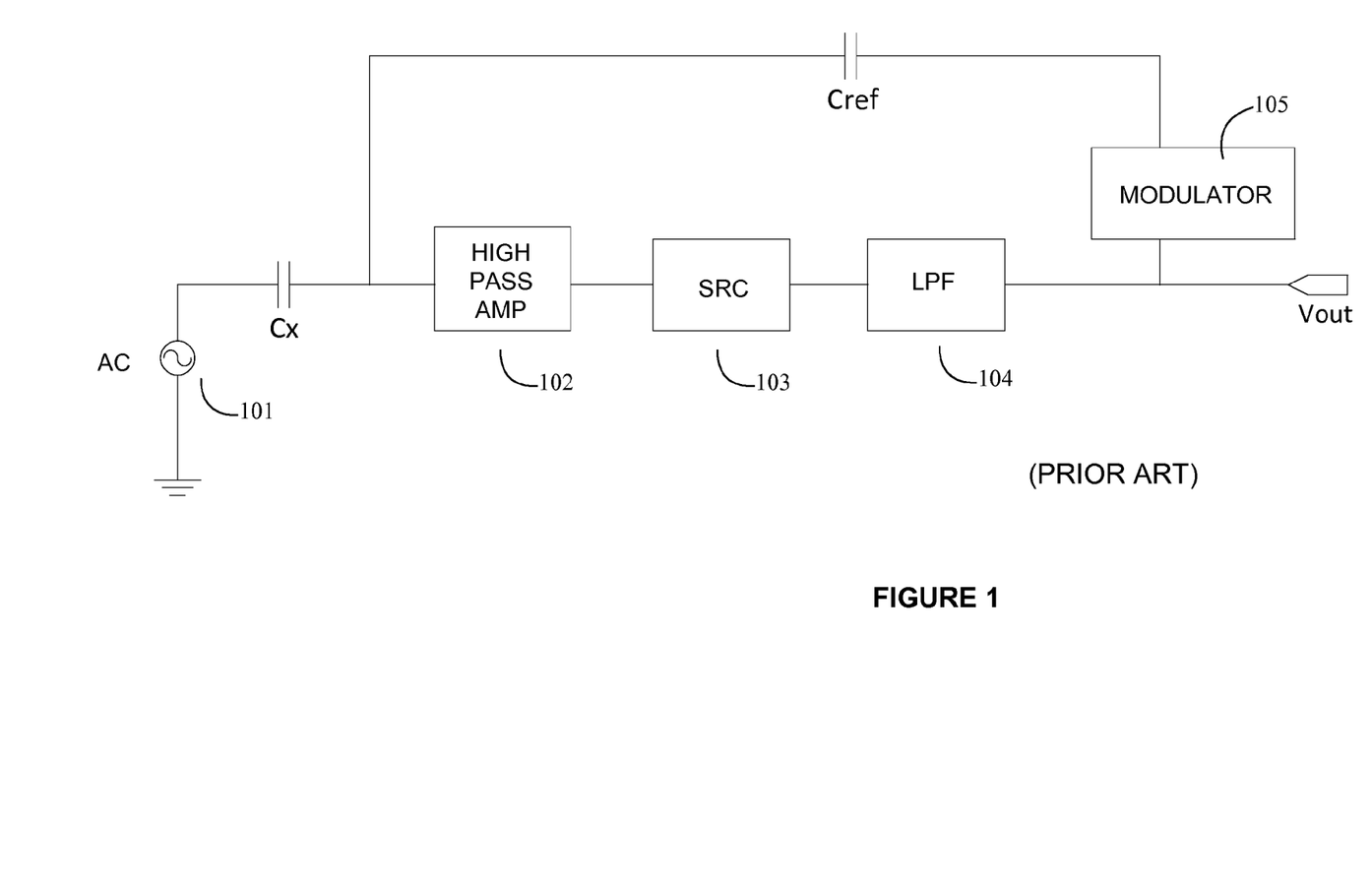
FIG. 1 is a circuit block diagram of a known CTLS circuit.

Output voltage Vout is modulated by a modulator circuit 105 to a square wave at the frequency of the AC signal generator 101 and synchronized thereto. The output of modulator circuit 105 is fed through a reference capacitor Cref back to the input of high pass amplifier 102. The modulator circuit 105 inverts the phase of the signal from the AC signal generator 101 so that the modulator circuit 105 and the AC signal generator 101 are 180 degrees out of phase with each other. The feedback loop controls output voltage Vout such that the input to high pass amplifier 102 is effectively a DC signal. In other words, the AC current through capacitor Cx is substantially balanced by the current through reference capacitor Cref. The transfer function for this circuit is $$V\text{out} = V_{AC} * Cx/\text{Cref},$$

where $V_{AC}$ is the voltage output of the AC signal generator 101. With Vout, $V_{AC}$ and Cref being known values, the capacitance of capacitor Cx can be determined which is indicative of the amount of toner existing in the toner container in which capacitor Cx is disposed. The circuit of FIG. 1 may be scaled to measure capacitors between about 0 pF and about 22 pF.

The absolute accuracy of the CTLS circuit is of importance in order to obtain accurate toner level measurements. If the CTLS circuit exceeds its error budget, the developer unit may either overfill or underfill. Overfill can cause the fill auger of the developer unit to break as it packs toner into the developer unit. Underfill can cause the developer unit to run dry which causes the doctor blade of the developer unit to undesirably strip a film off the developer roll. The error budget for the CTLS circuit of FIG. 1 may be less than 1.5 pF. Known error sources include: 1) a power supply that varies over time and temperature; 2) analog-to-digital circuitry characteristics (reference voltage, offset, non-linearity and gain), at least some of which may vary over time and temperature; 3) reference capacitor tolerance; 4) attenuation resistor tolerance; 5) operational amplifier offset voltage variation over time and temperature.

It is difficult to maintain the desired accuracy of the CTLS circuit with the above set of error sources. What is needed is a CTLS circuit with well controlled errors so the desired accuracy may be maintained.

SUMMARY

Example embodiments satisfy a need for a CTLS circuit that overcome the shortcomings of known circuits. According to an example embodiment, there is a system for determining the capacitance of a capacitor, such as a capacitive toner level sensor found in an imaging unit of an electrophotographic imaging device. The system may include at least one capacitor having a capacitance to be sensed, each at least one capacitor having a first terminal and a second terminal; a calibration capacitor having a first terminal and a second terminal; and first circuitry for sensing an input current at an input thereof and generating an output signal that is based upon a capacitance appearing at the input of the first circuitry. The system may further include multiplexer circuitry, coupled between the input of the first circuitry and the second terminal of each of the at least one capacitor and the calibration capacitor, for selectively coupling the second terminal of the at least one capacitor and the calibration capacitor, one at a time, to the input of the first circuitry while the second terminal not coupled to the input of the first circuitry is coupled to a ground reference; and controller circuitry for calculating a capacitance of the at least one capacitor based upon the output signal of the first circuitry when the at least one capacitor is coupled to the input thereof and upon the output signal of the first circuitry when the calibration capacitor is coupled to the input thereof. The multiplexer circuitry serves to improve the measurement accuracy by automatically calibrating with a known capacitance of the calibration capacitor. This allows for measuring very small capacitances without degrading the measurement accuracy. The multiplexer circuitry also reduces the cost of measuring multiple capacitances.

BRIEF DESCRIPTION OF THE DRAWINGS

The above-mentioned and other features and advantages of the disclosed embodiments, and the manner of attaining them, will become more apparent and will be better understood by reference to the following description of the disclosed embodiments in conjunction with the accompanying drawings, wherein.

DETAILED DESCRIPTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

Terms such as "first", "second", and the like, are used to describe various elements, regions, sections, etc. and are not intended to be limiting. Further, the terms "a" and "an" herein do not denote a limitation of quantity, but rather denote the presence of at least one of the referenced item.

Furthermore, and as described in subsequent paragraphs, the specific configurations illustrated in the drawings are intended to exemplify embodiments of the disclosure and that other alternative configurations are possible.

Reference will now be made in detail to the example embodiments, as illustrated in the accompanying drawings. Whenever possible, the same reference numerals will be used throughout the drawings to refer to the same or like parts.

Figure 2:
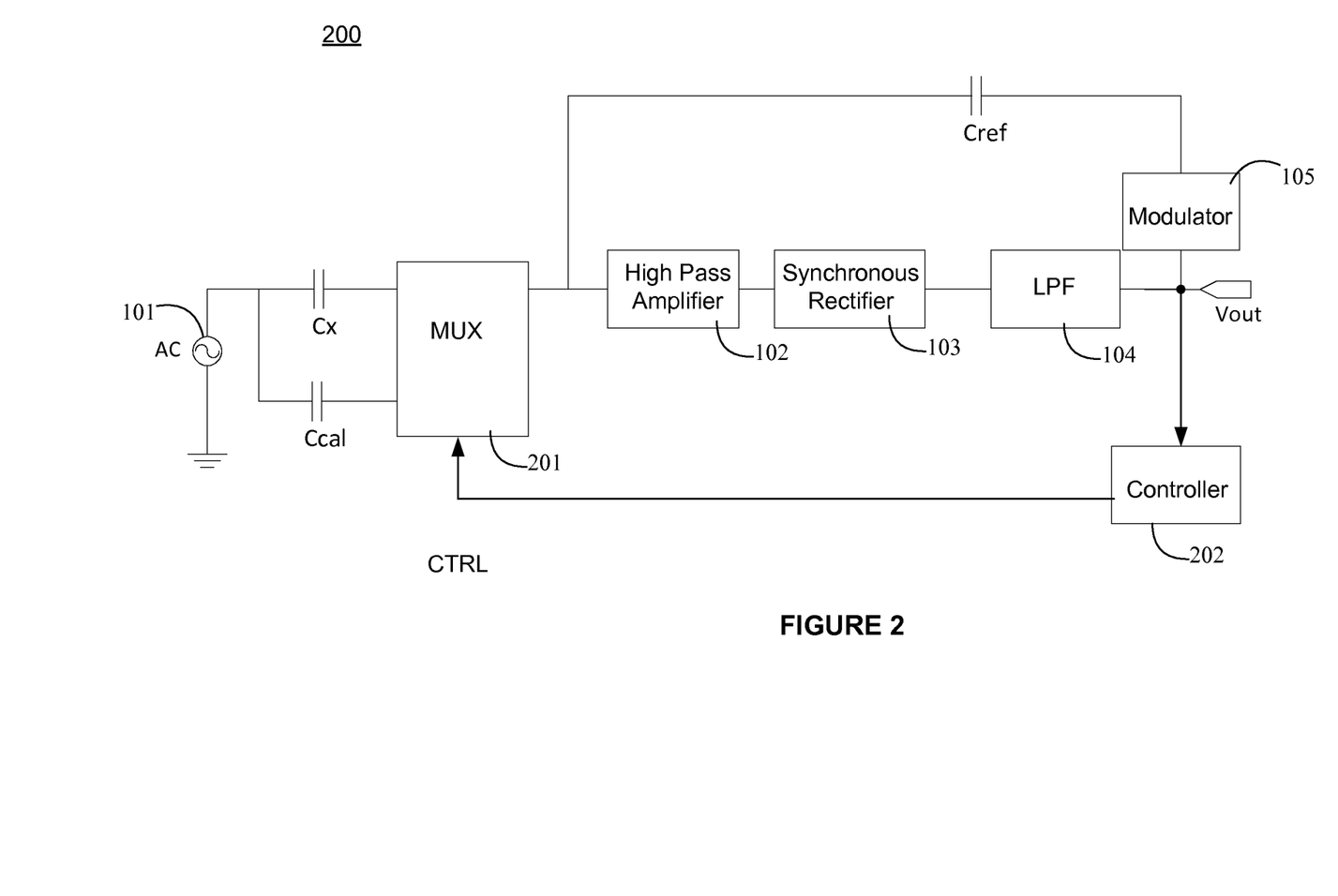
FIG. 2 is a circuit block diagram of a CTLS circuit according to example embodiments of the present disclosure.

According to an example embodiment, CTLS circuit accuracy can be better controlled by adding one or more calibration capacitors and a multiplexer to the CTLS circuit. A block diagram of the CTLS circuit 200 is shown in FIG. 2. The CTLS circuit 200 may be disposed within the imaging device, such as a printer, and be electrically coupled to the capacitive toner sensor Cx (shown in FIG. 2) whose capacitance is to be monitored. As can be seen, FIG. 2 includes the circuit of FIG. 1 as well as a multiplexer circuit 201. In general terms, multiplexer circuit 201 selectively couples to its output one of its inputs (capacitors Cx and Ccal) based upon the input control signal CTRL supplied to multiplexer circuit 201. Input control signal CTRL may be provided by a controller 202 of the imaging device which monitors and/or controls the operation of the imaging unit thereof. Controller 202 may be implemented as a processor or other processing and/or control circuitry.

Assume, for the sake of argument, that the multiplexer circuit 201 is ideal such that there is substantially zero parasitic capacitance across an unselected channel. In this case, controller 202 and CTLS circuit 200 can determine the capacitance of capacitor Cx by measuring the capacitance of calibration capacitor Ccal, measuring the capacitance of capacitor Cx, and using the calibration capacitor Ccal and Cx measurements to compute the actual capacitance of capacitor Cx by controller 202. For capacitance values of capacitor Cx that are near the capacitance of calibration capacitor Ccal, the accuracy of the CTLS circuit is generally the same as the accuracy of Ccal. It is much simpler (and less expensive) to control the accuracy of a single passive component than it is to control the accuracy of all the active and passive error sources.

The capacitance value of calibration capacitor Ccal was chosen to be the same as the capacitance of a half-full developer unit, i.e., the developer unit at its toner fill point. In operation, the accuracy of CTLS circuit 200 may be viewed as being most important at the developer unit fill point. Of course, alternatively a second calibration capacitor could be added for a two-point calibration to compensate for a range of capacitance values for capacitor Cx, and more than two calibration capacitors may be used to further compensate for the range of capacitance values for capacitor Cx.

Figure 3:
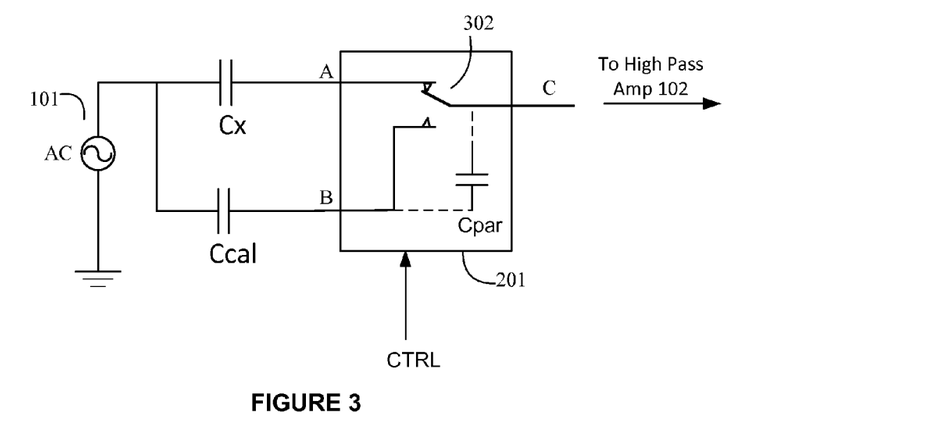
FIGS. 3-6 are circuit diagrams of the calibration circuitry of the CTLS circuit of FIG. 2 according to the example embodiments.

Unfortunately, real multiplexers are not ideal. There is parasitic capacitance that bridges open switches. Assume, for example, that the multiplexer circuit 201 is implemented as shown in FIG. 3. This is the traditional topology for a multiplexer, with output node C being connected to one of input nodes A and B via switch 302. The position of switch 302 is controlled by control signal CTRL. Note that the high-pass amplifier 102 described above is connected to node C. Here, the multiplexer circuit 201 either connects to the high pass amplifier 102 via nodal path A-C or nodal path B-C. Unfortunately, there is parasitic capacitance Cpar between nodes B and C. Thus, when path A-C is selected by control signal CTRL, the CTLS circuit 200 will measure not only capacitor Cx but also calibration capacitor Ccal in series with parasitic capacitor Cpar. As an example, a 74HCT4053 analog multiplexer typically has about 2 pF of capacitance connecting unselected inputs to the common output. Assuming calibration capacitor Ccal is about 15 pF, the 2 pF of parasitic capacitance Cpar will add about 1.75 pF of error to the measurement of capacitor Cx. Further, 2 pF is merely a typical value for the 74HC4053 and is not specified for worst case conditions/values.

Figure 4:
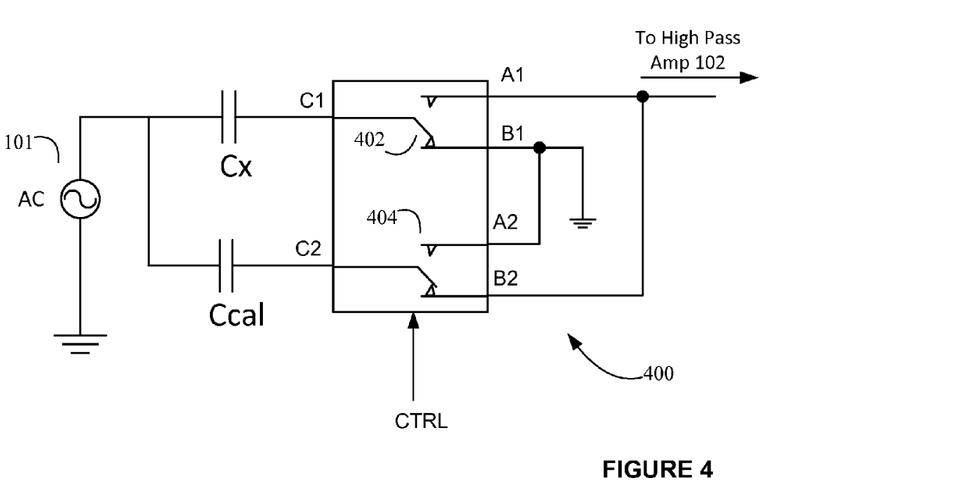

An improved multiplexer circuit 400 is shown in FIG. 4 according to an example embodiment. Multiplexer circuit 400 may include two analog switches 402 and 404. Analog switch 402 may have a first node C1 coupled to capacitor Cx, a second node A1 coupled to high pass amplifier 102 and a third node B1 coupled to the ground. Analog switch 404 may have a first node C2 coupled to calibration capacitor Ccal, a second node A2 coupled to ground and a third terminal B2 coupled to high pass amplifier 102. Analog switches 402 and 404 are controlled by control signal CTRL. In this way, when calibration capacitor Ccal is selected by control signal CTRL, the current through capacitor Cx is shunted to ground. Thus, the C1-B1 parasitic capacitance does not add error to the measurement and so does not provide additional error. Parasitic capacitances that may exist between nodes C1 and A1 and between nodes A1 and A2 also do not add error since the CTLS measurement circuit 200 is insensitive to the addition of tens of picofarads (pFs) of capacitance added between the input of the high-pass amplifier 102 and ground. This is because the AC voltage at that node is small and is seen equally by the capacitor Cx path and the capacitor Cref path.

Figure 5:
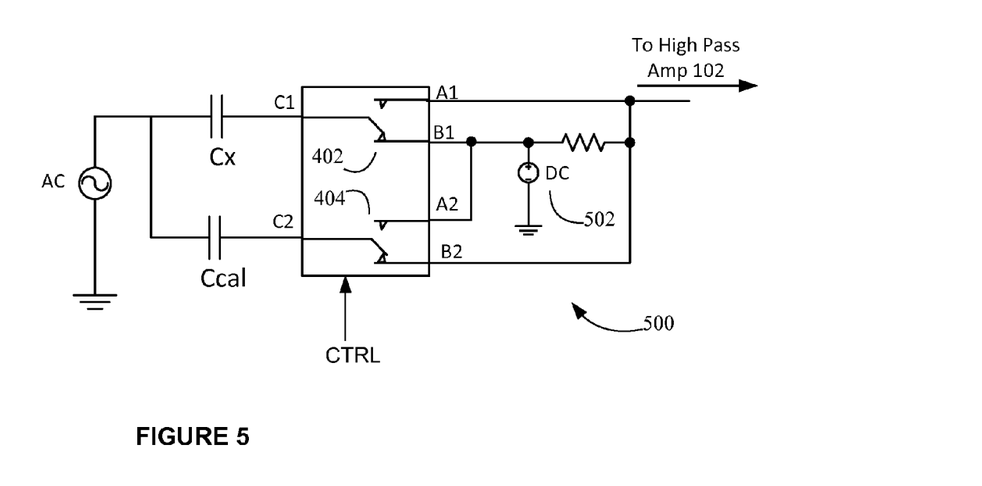

Another improved multiplexer circuit 500 is shown in FIG. 5 according to another example embodiment. Here, analog switches 402 and 404 are employed as they are in FIG. 4, with nodes C1 and A1 of analog switch 402 being coupled to capacitor Cx and high pass amplifier 012, respectively; and nodes C2 and B2 of analog switch 404 being coupled to calibration capacitor Ccal and high pass amplifier 102, respectively. In addition, node A1 of switch 402 and node B2 of switch 404 are coupled together. If the input of high-pass amplifier 102 is biased to a virtual ground, as described in U.S. patent application Ser. No. 13/432,693 identified above, it is advantageous to switch the unselected capacitor Cx and Ccal to virtual ground as well, as shown in FIG. 5. In particular, nodes B1 and A2 may be coupled to ground via a signal generator or power supply 502, which may be a DC signal generator. In this way, the channel-to-channel settling time is reduced since capacitors Cx and Ccal will always have approximately the same instantaneous voltage drop. This also maintains a substantially constant load on the AC excitation drive which helps keep the AC excitation waveform substantially constant which improves the accuracy of calibrating with calibration capacitor Ccal.

Figure 6:
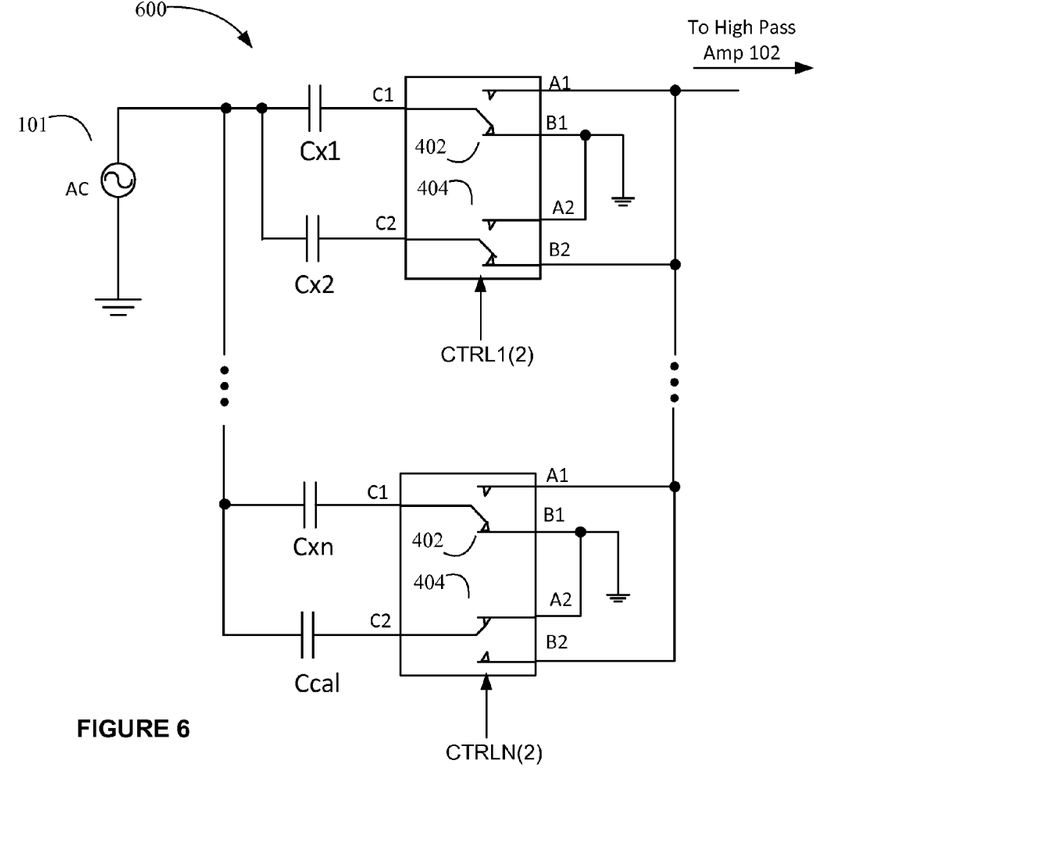

In addition to reducing errors, multiplexing also allows a single measurement circuit to measure multiple unknown capacitances. An example multiplexer circuit 600 is shown in FIG. 6. Multiplexer circuit 600 may include multiple instances of parallel-connected multiplexer circuit 400 of FIG. 4, with each multiplexer circuit 400 being coupled between at least one capacitor Cx needing to be measured and high pass amplifier 102. Multiplexer circuit 600 may be utilized, for example, in a color electrophotographic imaging device having four sets of toner cartridges and imaging units. In this case, capacitor Cx1 corresponds to the capacitive toner sense capacitor for a cyan developer unit, capacitor Cx2 corresponds the sense capacitor for a magenta developer unit, a capacitor Cx3 (not shown) would likewise correspond to the capacitive sensor for a yellow developer unit, and a capacitor Cx4 (not shown) would correspond to the capacitive sensor for a black developer unit. Alternatively, each capacitor Cx could represent the capacitance across a distinct ink tank in an inkjet printer. All capacitors Cx may share a common calibration capacitor Ccal and share a common high pass amplifier circuit 102, synchronous rectifier 103, low pass filter 104, modulator 105 and reference capacitor Cref (not shown in FIG. 7). In multiplexer circuit 600, each analog switch 402, 404 connecting each capacitor Cx or Ccal to the output (to the common high pass amplifier circuit 102) may be individually controlled, such that each pair of analog switches 402, 404 may be controlled by a pair of control signals CTRL. The shared circuitry and components reduce system cost compared to the use of redundant circuits and components for each capacitor Cx. Since multiplexer circuit 600 does not add accuracy errors, any number of capacitors Cx to be sensed may be multiplexed as needed.

It is understood that in an alternative embodiment, multiplexer circuit 600 may include a plurality of parallel-connected multiplexer circuits 500 instead of multiplexer circuits 400 illustrated in FIG. 6.

The operation of multiplexer circuits 400, 500 and 600 will be described with reference to FIG. 7 for determining the actual capacitance of capacitive toner sensor Cx. At 702, capacitive sensor Cx may be coupled, and calibration capacitor Ccal decoupled, between AC source 101 and high pass amplifier 102. This may be performed by controlling analog switches 402, 404 using control signal CTRL so as to select nodal path C1-A1. The capacitance of Cx may then be measured at 704 using the circuitry shown in FIG. 2, i.e., high pass amplifier circuit 102, synchronous rectifier 103, low pass filter 104, modulator 105 and reference capacitor Cref as described above. Capacitive toner sensor Cx may then be decoupled from, and calibration capacitor Ccal thereby coupled between, AC source 101 and high pass amplifier 102 at 706 using control signal CTRL. Thereafter, the capacitance of calibration capacitor Ccal may be measured at 708 using the circuitry of FIG. 2 as described above. With the capacitance measurements for capacitors Cx and Ccal, the actual and/or calibrated capacitance of Cx may be determined at 710 by controller 202 based upon the capacitance measurements for capacitors Cx and Ccal.

Figure 7:
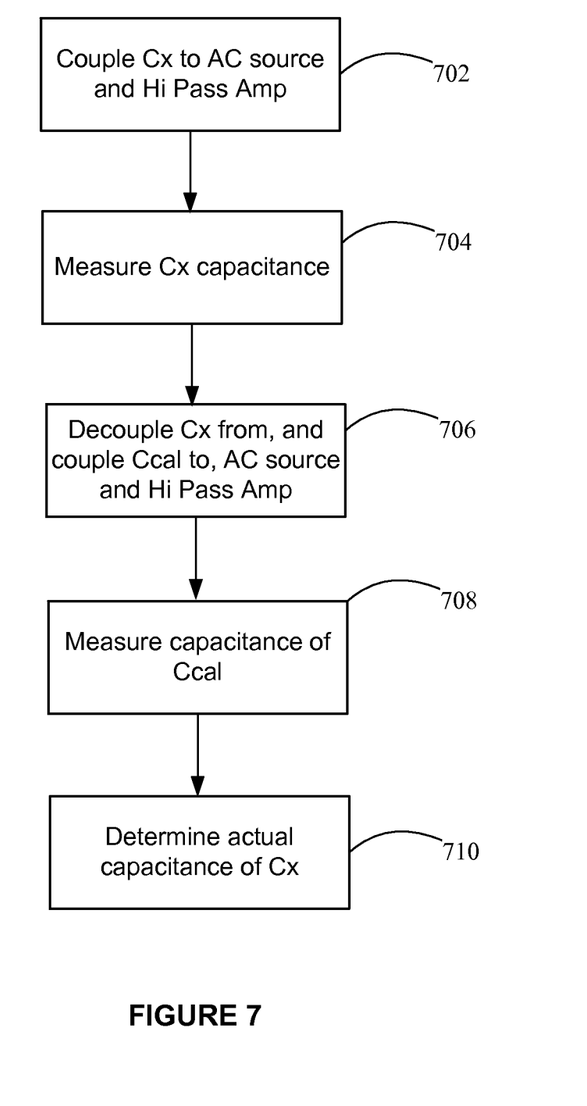
FIG. 7 is a flow chart illustrating the operation of the circuit of FIG. 2 according to an example embodiment.

It is understood that the above described acts of FIG. 7 may appear in a different order. For example, the capacitance of calibration capacitor Ccal may be measured before the capacitance of capacitor Cx is measured.

The foregoing description of several methods and embodiments has been presented for purposes of illustration. It is not intended to be exhaustive or to limit the disclosure to the precise acts and/or forms disclosed, and obviously many modifications and variations are possible in light of the above teaching. It is intended that the scope of the invention be defined by the claims appended hereto.

I claim:

1. A system for determining capacitance of a capacitor, comprising:
   at least one first capacitor having a capacitance to be sensed, each at least one first capacitor having a first terminal and a second terminal;
   a first signal generator coupled to the first terminal of the at least one first capacitor for generating an alternating signal;
   a second capacitor having a first terminal coupled to the signal generator and a second terminal;
   a conversion circuitry for sensing an alternating current at an input thereof and generating a substantially DC voltage output signal based upon the sensed alternating current; and
   a switching circuitry, coupled between the input of the conversion circuitry and the second terminal of each of the at least one first capacitor and the second capacitor, for selectively coupling the second terminal of the at least one first capacitor and the second capacitor, one at a time, to the input of the conversion circuitry while the second terminal not coupled to the input of the conversion circuitry is coupled to a ground reference, the substantially DC voltage output signal of the conversion circuitry being based upon a capacitance of the capacitor coupled to the input of the conversion circuitry.

2. The system of claim 1, wherein the at least one first capacitor comprises a plurality of first capacitors, each first capacitor having a first terminal coupled to the signal generator and a second terminal, and wherein each second terminal not coupled to the input of the conversion circuitry is coupled to the ground reference.

3. The system of claim 1, wherein each second terminal of the at least one first capacitor and the second capacitor not coupled to the input of the conversion circuitry is coupled to the ground reference through a second signal generator.

4. The system of claim 3, wherein the second signal generator is a DC signal generator.

5. The system of claim 4, wherein the switching circuitry further comprises at least one resistor coupled between the second signal generator and the input of the conversion circuitry.

6. The system of claim 1, further comprising processing circuitry coupled to the conversion circuitry for determining a capacitance of the at least one first capacitor based in part upon the substantially DC voltage output signal from the conversion circuitry when the at least one first capacitor and the second capacitor are coupled to the input of the conversion circuitry.

7. The system of claim 6, wherein the processing circuitry controls the switching circuitry to selectively couple one of the at least one first capacitor and the second capacitor to the input of the conversion circuitry, one at a time.

8. The system of claim 1, wherein the switching circuitry comprises a plurality of analog switches, each analog switch coupled between a distinct one of the at least one first capacitor and the second capacitor and the input of the conversion circuitry.

9. The system of claim 8, further comprising controller circuitry, wherein a control terminal of each analog switch is coupled to a control signal driven by the controller circuitry.

10. The system of claim 1, wherein the second capacitor comprises a calibration capacitor.

11. A system for determining the capacitance of a capacitor, comprising:
    at least one first capacitor having a capacitance to be sensed, each at least one first capacitor having a first terminal and a second terminal;
    a second capacitor having a first terminal and a second terminal;
    a first circuitry for sensing an input current at an input thereof and generating an output signal that is based upon a capacitance appearing at the input of the first circuitry;
    a multiplexer circuitry, coupled between the input of the first circuitry and the second terminal of each of the at least one first capacitor and the second capacitor, for selectively coupling the second terminal of the at least one first capacitor and the second capacitor, one at a time, to the input of the first circuitry while the second terminal not coupled to the input of the first circuitry is coupled to a ground reference; and
    a controller circuitry for calculating a capacitance of the at least one first capacitor based upon the output signal of the first circuitry when the at least one first capacitor is coupled to the input thereof and upon the output signal of the first circuitry when the second capacitor is coupled to the input thereof.

12. The system of claim 11, wherein the at least one first capacitor comprises a plurality of first capacitors, each first capacitor having a first terminal and a second terminal, and wherein each second terminal not coupled to the input of the first circuitry is coupled to the ground reference.

13. The system of claim 11, wherein each second terminal of the at least one first capacitor and the second capacitor not coupled to the input of the first circuitry is coupled to the ground reference through a signal generator.

14. The system of claim 13, wherein the multiplexer circuitry includes at least one resistor coupled between the signal generator and the input of the first circuitry.

15. The system of claim 11, wherein the multiplexer circuitry comprises a plurality of analog switches, each analog switch coupled between a distinct one of the at least one first capacitor and the second capacitor and the input of the first circuitry.

16. The system of claim 11, wherein a control terminal of each analog switch is coupled to a control signal driven by the controller circuitry.

17. The system of claim 11, further comprising a signal generator having an output coupled to the first terminal of each at least one first capacitor and the second capacitor.

18. The system of claim 17, wherein the signal generator is an AC signal generator for generating an AC signal, and the first circuitry senses an AC signal appearing at the input thereof.

19. The system of claim 11, wherein the second capacitor comprises a calibration capacitor.

* * * * *